United States Patent [19]

Take

[11] Patent Number: 5,117,639
[45] Date of Patent: Jun. 2, 1992

[54] AUTOMATIC COOLING SYSTEM

[75] Inventor: Masafumi Take, Tokyo, Japan

[73] Assignee: Seiko Instruments, Inc., Tokyo, Japan

[21] Appl. No.: 521,331

[22] Filed: May 9, 1990

[30] Foreign Application Priority Data

May 10, 1989 [JP] Japan .................. 1-116577

[51] Int. Cl.⁵ .................................. F17C 7/04
[52] U.S. Cl. ........................... 62/48.1; 219/497; 236/78
[58] Field of Search ............... 236/78; 219/497, 510; 62/48.1

[56] References Cited

FOREIGN PATENT DOCUMENTS 1180657  9/1985  U.S.S.R. .................. 62/48.1
1259226  9/1986  U.S.S.R. .................. 236/78

Primary Examiner—William E. Wayner
Attorney, Agent, or Firm—Spensley Horn Jubas & Lubitz

[57] ABSTRACT

A system for controlling the heater of a liquid nitrogen vaporization type cooling system includes a heater power computer circuit, a comparator, a synchronizing pulse generating circuit, an integrating circuit and a relay for automating the heater control to adjust the vaporization rate of the liquid nitrogen automatically.

3 Claims, 1 Drawing Sheet

AUTOMATIC COOLING SYSTEM

BACKGROUND OF THE INVENTION

The present invention relates to a cooling system for use when a cold region is to be measured by a thermal analyzer.

A measurement technique of this kind used in the prior art is exemplified either by a manual adjustment using a Slidac or by a control using only the heating furnace of a thermal analyzer, while holding the vaporization rate of liquid nitrogen at a constant value.

The above-specified prior art has to either perform measurements while requiring the operator to adjust the Slidac or has to keep a temperature at all times, leading to a consumption of a considerable quantity of liquid nitrogen.

The present invention has been conceived to solve such problems and to provide a system able to perform the cooling operation in accordance with the output of the heater power computing circuit.

SUMMARY OF THE INVENTION

An object of the present invention is to eliminate the above-specified drawbacks and provide an automatic cooling system which comprises: a heater power computing circuit; a comparator for receiving the output of the heater power computing circuit as one input; a synchronizing pulse generating circuit for generating the synchronizing pulses of an AC power source; an integration circuit for integrating the outputs of the synchronizing pulse generating circuit and outputting an integrated value to the other input of the comparator; and a relay for turning on and off the power to a heater in response to the output of the comparator.

In the operation of the above-specified structure, the temperature of a heating furnace of the thermal analyzer and a target temperature are inputted at first to the heater power computing circuit. This heater power computing circuit computes the electric power to be supplied to the heater and outputs it to one input of the comparator. The synchronizing pulse generating circuit generates pulses synchronized with the AC power source and inputs them to the integration circuit. This integration circuit integrates the synchronizing pulses and outputs their values to the other input of the aforementioned comparator. Here, the aforementioned integration circuit is designed to restore a zero level in case the integrated value reaches its upper limit. The aforementioned comparator compares the two inputs to turn on the relay if the input from the heater power computing circuit is higher, then turns off the relay if the input from the integration circuit is higher.

The comparator always compares the two inputs to turn on the relay, thereby to supply the heater with electric power to vaporize the liquid nitrogen, while the input from the aforementioned integration circuit is lower than that from the aforementioned heater power computing circuit in case the input from the aforementioned heater power computing circuit is constant. In case the input from the aforementioned integration circuit exceeds the input from the aforementioned heater power computing circuit, the comparator turns off the relay to supply the heater with no electric power thereby to stop vaporization of the liquid nitrogen. Thus, there is achieved an action for adjusting the vaporization rate of the liquid crystal according to the output of the aforementioned heater power computing circuit.

DETAILED DESCRIPTION OF THE PREFERRED EMBODIMENTS

Figure 1:
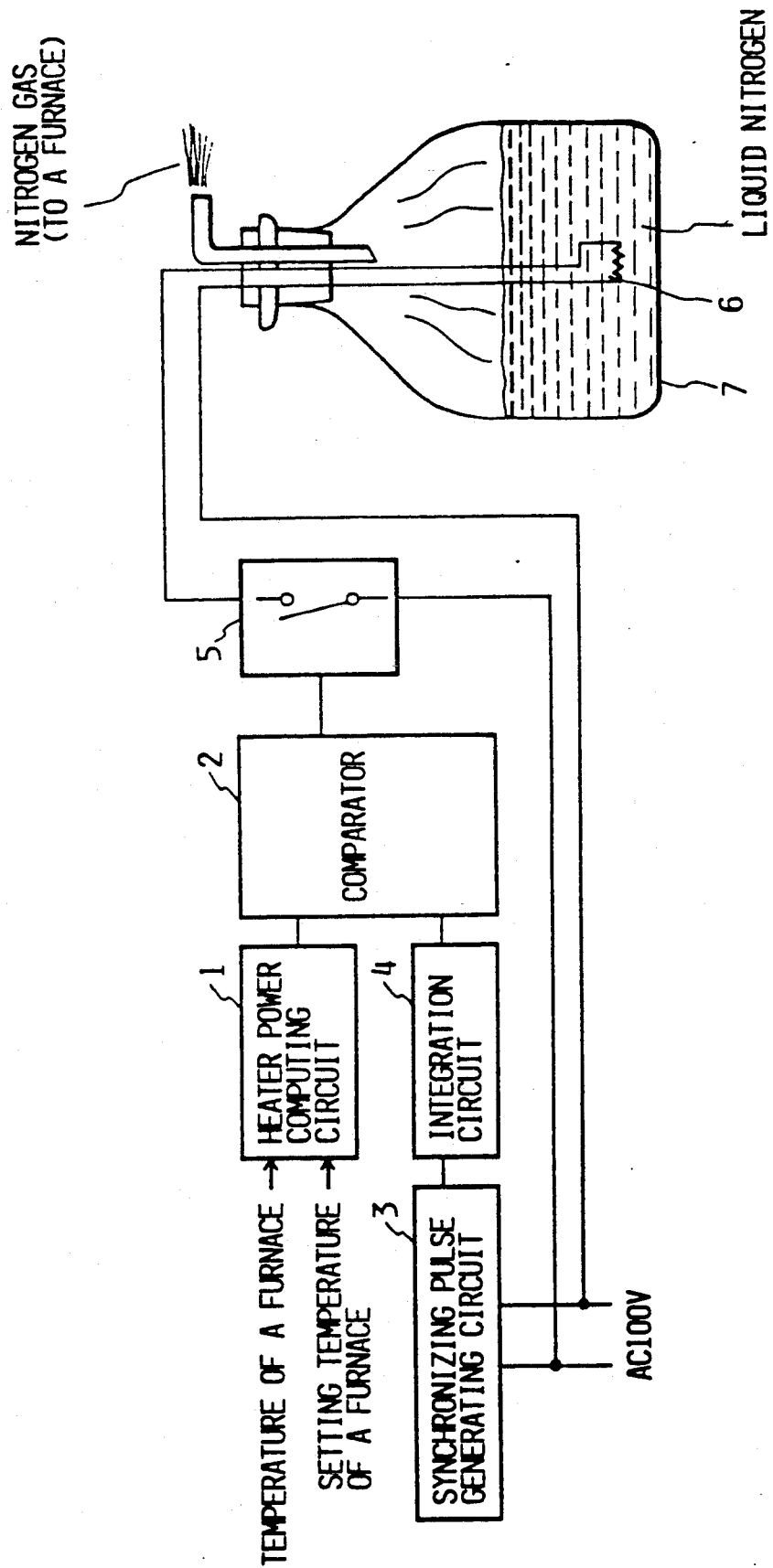
FIG. 1 is a block diagram showing one embodiment of a system according to the present invention.

The present invention will be described in detail in the following in connection with one embodiment thereof with reference to the accompanying drawing.

FIG. 1 shows a heater power computing circuit 1 which is fed with signals representing the temperature of a heating furnace and its target temperature. The aforementioned heater power computing circuit computes an 8-bit digital signal having range from 1 to 255 to one input of a comparator 2. A synchronizing pulse generating circuit 3 generates pulses synchronized with the AC power for heater 6 to input those pulses to an integration circuit 4. This integration circuit 4 also performs integrations to produce an 8-bits word ranging in value from 0 to 255 and outputs the integrated value to the other input of the comparator 2. The value 255 is represented in binary form by 8 ones. When such a digital circuit is in a state in which all of its outputs are ones, the next pulse received from circuit 3 will cause the 8-bits of the word produced by circuit 4 to be all zeros. As a result the output of integration circuit 4 returns from a value of 255 to zero. The aforementioned comparator 2 compares the two inputs to turn on, or close a relay 5, if the input from the heater power computing circuit 1 is higher, and turns relay 5 off if the input from integration circuit 4 is higher.

In case the input from heater power computing circuit 1 to comparator 2 is constant, relay 5 is turned on while the input from integration circuit 4 to comparator 2 is lower than that from heater power computing circuit 1, so that the electric power is supplied to the heater 6 to vaporize the liquid nitrogen for the cooling operations. In case the input from integration circuit 4 exceeds the input from heater power computing circuit 1, the relay 5 is turned off to stop the power supply to heater 6 so that the liquid nitrogen is not vaporized any more to stop the cooling operations. At the beginning of a given cycle, the output signal from circuit 1 will be greater than that from circuit 4. At some point in time, the digital signal from circuit 4 will exceed that from circuit 1, at which time relay 5 is turned off to stop the power supply to heater 6. Thus, during each cycle, the length of time during which relay 5 is closed will be proportional to the magnitude of the output signal from circuit 1. If this output signal has a high value, then a longer period of time will elapse before the output signal from integrator circuit 4 exceeds that from circuit 1. If the output signal from circuit 1 has a low value, a shorter period of time will elapse before the output signal from circuit 4 exceeds that produced by circuit 1. As a result, the cooling operations are performed according to the output of heater power computing circuit 1.

As has been described hereinbefore, according to the present invention, cooling operations can be performed according to the output of heater power computing circuit 1 so that they are automatically accomplished to reduce the consumption of liquid nitrogen. In the illustrated embodiment, moreover, the present invention has been implemented by a digital circuit, but can be implemented by an analog circuit. It goes without saying that heater power computing circuit 1 can be constructed of a microprocessor.

I claim:

1. An automatic cooling system comprising:
an electrically-powered heater for generating heat to vaporize a cooling medium serving to cool a region;
a heater power computing circuit for providing an output signal having a value representing the difference between the actual temperature and the desired temperature of the region to be cooled; means for supplying AC power; pulse generating means corrected to generate pulses at a frequency corresponding to the frequency of the AC power; integrating means connected to said pulse generating means for producing an output signal having a value representative of the integral of the pulses produced by said pulse generating means; a comparator having inputs connected to receive the output signals from said computing circuit and said integrating means and having an output for providing a signal when the signal value at a selected one of the inputs is greater than the signal value at the other one of the inputs; and switching means connected to the means for supplying AC power and to said heater and operatively coupled to the output of said comparator for supplying AC power to said heater during times when a signal is provided at said comparator output.

2. A system as defined in claim 1 further comprising a container, and a mass of liquid which condenses at a low temperature, which liquid constitutes the cooling medium, said heater being disposed for vaporizing said liquid.

3. A system as defined in claim 2 wherein the liquid is liquid nitrogen.

* * * * *